(12) United States Patent
Musho et al.

(10) Patent No.: US 9,662,301 B2
(45) Date of Patent: May 30, 2017

(54) PRODUCTION OF UNIT DOSE CONSTRUCTS

(71) Applicant: ARx, LLC, Glen Rock, PA (US)

(72) Inventors: Matthew K. Musho, York, PA (US); John H. Lind, York, PA (US); Scott D. Barnhart, York, PA (US)

(73) Assignee: ARX, LLC, Glen Rock, PA (US)

( * ) Notice: Subject to any disclaimer, the term of this patent is extended or adjusted under 35 U.S.C. 154(b) by 0 days.

(21) Appl. No.: 15/371,915

(22) Filed: Dec. 7, 2016

(65) Prior Publication Data

US 2017/0087097 A1     Mar. 30, 2017

Related U.S. Application Data

(63) Continuation of application No. 14/161,829, filed on Jan. 23, 2014, now Pat. No. 9,545,376.

(60) Provisional application No. 61/755,495, filed on Jan. 23, 2013, provisional application No. 61/755,492, filed on Jan. 23, 2013.

(51) Int. Cl.
   *A61K 9/00*     (2006.01)
   *A61K 9/70*     (2006.01)

(52) U.S. Cl.
   CPC ............ *A61K 9/7007* (2013.01); *A61K 9/006* (2013.01)

(58) Field of Classification Search
   CPC .............................. A61K 9/006; A61K 9/7007
   See application file for complete search history.

(56) References Cited

U.S. PATENT DOCUMENTS

| | | |
|---|---|---|
| 3,444,858 A | 5/1969 | Russell |
| 4,029,757 A | 6/1977 | Mlodozeniec et al. |
| 4,128,445 A | 12/1978 | Sturzenegger et al. |
| 4,136,162 A | 1/1979 | Fuchs et al. |
| 4,197,289 A | 4/1980 | Sturzenegger et al. |
| 4,451,260 A | 5/1984 | Mitra |
| 4,483,846 A | 11/1984 | Koide et al. |
| 4,925,670 A | 5/1990 | Schmidt |
| 5,188,838 A | 2/1993 | Deleuil et al. |
| 5,384,124 A | 1/1995 | Courteille et al. |
| 5,650,192 A | 7/1997 | Britton et al. |
| 5,763,476 A | 6/1998 | Delbressine et al. |
| 5,806,284 A | 9/1998 | Gifford |
| 6,280,771 B1 | 8/2001 | Monkhouse et al. |
| 6,596,298 B2 | 7/2003 | Leung et al. |
| 6,648,958 B2 | 11/2003 | Anselmann et al. |
| 6,783,768 B1 | 8/2004 | Brown et al. |
| 7,357,891 B2 | 4/2008 | Yang et al. |
| 7,425,292 B2 | 9/2008 | Yang et al. |
| 7,470,397 B2 | 12/2008 | Meathrel et al. |
| 7,910,641 B2 | 3/2011 | Myers |

(Continued)

FOREIGN PATENT DOCUMENTS

| | | |
|---|---|---|
| EP | 0386688 A1 | 12/1990 |
| WO | 03/030881 A1 | 4/2003 |

(Continued)

*Primary Examiner* — Timothy Kennedy
(74) *Attorney, Agent, or Firm* — McNees Wallace & Nurick LLC (57) ABSTRACT

Dissolvable unit dose constructs and their method of manufacture are disclosed in which the unit dose constructs are formed of a composition including a polymer matrix that includes a water soluble polymer, active ingredient, and a liquid carrier. The composition is deposited directly, such as by stenciling, to form individual unit doses without the need to cut and convert long, continuous rolls of film.

14 Claims, 4 Drawing Sheets

(56) References Cited

U.S. PATENT DOCUMENTS

| | | |
|---|---|---|
| 7,993,674 B2 | 8/2011 | Weibel |
| 2004/0241242 A1 | 12/2004 | Fuisz et al. |
| 2005/0048102 A1 | 3/2005 | Tapolsky et al. |
| 2005/0074490 A1 | 4/2005 | Lin et al. |
| 2007/0031477 A1 | 2/2007 | Fotinos et al. |
| 2008/0124381 A1 | 5/2008 | Barnhart et al. |
| 2009/0047330 A1 | 2/2009 | Bangalore |
| 2009/0196907 A1 | 8/2009 | Bunick et al. |
| 2009/0241483 A1 | 10/2009 | Detwiler et al. |
| 2010/0080829 A1 | 4/2010 | Dulieu et al. |
| 2011/0010817 A1 | 1/2011 | Theberge et al. |
| 2011/0196525 A1 | 8/2011 | Bogue |
| 2012/0076921 A1 | 3/2012 | Myers et al. |
| 2012/0100202 A1 | 4/2012 | Bogue |
| 2012/0207929 A1 | 8/2012 | Yoo et al. |

FOREIGN PATENT DOCUMENTS

| | | |
|---|---|---|
| WO | 03/030882 A1 | 4/2003 |
| WO | 03/030883 A1 | 4/2003 |

PRODUCTION OF UNIT DOSE CONSTRUCTS

CROSS-REFERENCE TO RELATED APPLICATIONS

This application is a continuation of U.S. application Ser. No. 14/161,829 filed Jan. 23, 2014 which claims the benefit of, and priority to, U.S. Prov. App. Nos. 61/755,495 and 61/755,492, both of which were filed on Jan. 23, 2013, and all of which are hereby incorporated by reference in their entirety.

FIELD

The present application is directed toward the field of drug delivery and more particularly to methods of producing unit dose constructs for drug delivery.

BACKGROUND

Fast-dissolving drug-delivery systems were first developed in the late 1970s as an alternative to tablets, capsules and syrups for pediatric, geriatric and other patients who experience difficulties swallowing traditional oral solid-dosage forms. In response to this need, a variety of orally disintegrating tablet (ODT) formats were commercialized. Most ODT products were formulated to dissolve in less than one minute when exposed to saliva to form a solution that could then be more easily swallowed.

More recently, dissolvable oral thin films (OTFs) emerged from the confection and oral care markets in the form of breath strips. These products became a widely accepted form by consumers for delivering vitamins and personal care products and subsequently for also delivering other active ingredients, including pharmaceuticals.

Pharmaceutical companies and consumers alike have embraced OTFs as a practical and accepted alternative to traditional medicine forms such as liquids, tablets, and capsules. OTFs offer fast, accurate dosing in a safe, efficacious format that is convenient and portable, without the need for water or measuring devices. OTFs are typically the size of a postage stamp and disintegrate on a patient's tongue in a matter of seconds for the rapid release of one or more active pharmaceutical ingredients (APIs). More broadly, the use of thin films has expanded to include a variety of products that are manufactured and used for a wide range of transmucosal drug delivery within the oral cavity as well as via other mucosal interfaces.

Known methods of dissolvable film production involve casting the liquid formulation as a continuous film, sheet or web in the form of wide and long rolls on a continuous substrate (e.g. paper or polyester liners which may or may not have release coatings) to form what is sometimes referred to as a master roll. The manufacturing process includes drying the liquid formulation to remove solvents (aqueous and/or non-aqueous) to yield the thin film on the substrate. The master rolls thus formed are then converted into smaller unit doses through a combination of roll slitting and individual unit dose die-cutting, as well as transferring those doses from the manufacturing substrate to the product's primary packaging.

Despite the move toward drug delivery by dissolvable tablets and films, numerous drawbacks and disadvantages still exist with such products and there are a variety of commercial needs in the field that have not yet been met.

SUMMARY

Exemplary embodiments are directed to dissolvable unit dose constructs for transmucosal drug delivery (oral and otherwise) including, but not limited to, dissolvable films, wafers and tablets and the production of the same that address currently existing, but unmet needs. More particularly, exemplary embodiments are directed to improvements relating to unit dose manufacture of those constructs.

According to an exemplary embodiment, a method of forming a dissolvable unit dose construct comprises providing a muco-adhesive composition comprising a polymer matrix, the polymer matrix comprising a water soluble polymer, the composition further comprising an active ingredient and a liquid carrier, the composition in the form of a thixotropic paste; stenciling the paste onto a substrate to deposit the composition as a plurality of individual dosage units; and removing at least a portion of the liquid carrier from the individual dosage units.

According to another exemplary embodiment, a method of forming a dissolvable unit dose construct comprises providing a muco-adhesive composition comprising a polymer matrix, the polymer matrix comprising a water soluble polymer, the composition further comprising an active ingredient and a liquid carrier; depositing the composition onto a substrate as a plurality of individual dosage units; and vacuum drying the individual dosage units to remove at least a portion of the liquid carrier.

According to yet another exemplary embodiment, a method of forming a dissolvable unit dose construct comprises providing a first composition comprising a water soluble polymer and a liquid carrier; depositing the first composition onto a substrate; providing a second composition comprising a water soluble polymer and a liquid carrier; stenciling the second composition at a plurality of discrete locations overlying the first composition; and removing at least a portion of the liquid carrier from the first and second compositions to form a multi-layer unit dose construct.

According to still another exemplary embodiment, a method of forming a dissolvable unit dose construct comprises providing at least one muco-adhesive composition comprising a polymer matrix, the polymer matrix comprising a water soluble polymer, the composition further comprising an active ingredient and a liquid carrier; depositing the composition onto a substrate as a first individual dosage unit; depositing a second individual dosage unit onto the substrate adjacent the first individual dosage unit; and removing liquid carrier from the individual dosage units, wherein the first and second individual units are distinct from one another in volume, composition, or other physical or chemical property.

According to still another exemplary embodiment, a method of forming a dissolvable unit dose construct comprises providing a first composition comprising a water soluble polymer and a liquid carrier; depositing the first composition onto a substrate to form a plurality of individual units; providing a second composition comprising a water soluble polymer, an active ingredient and a liquid carrier; depositing the second composition overlying a portion of an individual unit of the first composition; providing a third composition comprising a water soluble polymer, an active ingredient of an identity different from the active ingredient of the second composition, and a liquid carrier; depositing the third composition overlying a portion of the individual unit of the first composition different from the portion overlain by the second composition; and removing at least a portion of the liquid carrier from the compositions to form a multi-layer unit dose construct.

An advantage of certain exemplary embodiments includes that the use of individually formed doses limits variation of the active ingredient between dosage units. Particularly in the case of stenciling, advantages include the ability to deliver readily an appropriate deposit thickness for the construct being formed. Openings in the stencil mask define a volume of paste with which the openings in the stencil are filled and provides a more uniform deposit of the construct formulation. The use of stenciling also permits the use of a more viscous formulation, such as a thixotropic paste. As a result, a wider variety of constructs can be created, as the paste is better able to hold its shape enabling the formation of thicker individually formed unit does constructs including wafers and tablets, in addition to films.

Another advantage of certain exemplary embodiments is that vacuum drying in unit dose construct production can provide faster drying times at lower temperatures that, in-turn, affords improved productivity, lower energy consumption and improved stability, as well as reducing potential for entrapped air or bubble defects. The combination of cooling with vacuum drying can also yield a lyophilization effect.

Another advantage of certain exemplary embodiments includes that the ability to place different size active areas on a commonly sized backing layer using the same production equipment across production runs or even within the same production run.

An advantage of certain exemplary embodiments includes the ability to generate multiple adjacent constructs of different levels or types of active for in-line production of a drug regimen as a group of dissolvable films or other unit dose construct.

Still another advantage of certain exemplary embodiments includes the ability to incorporate multiple actives into a single unit dose construct, even if those active ingredients would otherwise be incompatible with one another, through discrete deposition of those active ingredients at separate locations on a common carrier.

Other features and advantages of the present invention will be apparent from the following more detailed description of exemplary embodiments, taken in conjunction with the accompanying drawings which illustrate, by way of example, the principles of the invention.

DETAILED DESCRIPTION OF EXEMPLARY EMBODIMENTS

Exemplary embodiments are directed to unit dosage forms for oral and other transmucosal drug delivery. While described primarily with respect to films, and more particularly those constructs known within the art as thin films (films having a thickness between 0.1 mils and 10 mils), other dissolvable muco-adhesive constructs are also contemplated by the present disclosure and the exemplary embodiments described herein. Such additional unit dose constructs include, without limitation, thick films (films having a thickness greater than 10 mils), wafers and tablets.

The composition of the films and other unit dose constructs discussed in the context of exemplary embodiments can be characterized broadly as a liquid-base biologically compatible muco-adhesive polymer matrix containing an active ingredient that forms an erodible, disintegrable and/or dissolvable construct upon drying and may include, without limitation, the films described in U.S. Pat. No. 7,470,397, which is incorporated by reference in its entirety. It will be appreciated that the resulting constructs have a combination of a solid content sufficient to provide strength to aid in handling but balanced to provide disintegration at a predetermined rate.

Any suitable polymers may be employed as the matrix of the unit dose constructs in accordance with exemplary embodiments. It will be appreciated that the polymer(s) selected for any particular construct may depend on a variety of factors, including the active ingredient to be incorporated, the desired rate of disintegration (which may be modified with or without the use of a surfactant), and the rheology of the liquid formulation, as well as other factors known to those of ordinary skill in the art for producing conventional drug delivery constructs.

The polymer(s) may be water soluble, water swellable, water insoluble, or a combination thereof and may include cellulose or a cellulose derivative. Although the use of water swellable and water insoluble polymers is contemplated, the formulation contains a sufficient amount of water soluble polymer to ensure the eventual disintegration of the subsequently formed film.

Exemplary polymers for the muco-adhesive matrix include water-soluble hydroxypropylmethyl cellulose, hydroxyethyl cellulose, hydroxypropyl cellulose, polyvinyl pyrrolidone, carboxymethyl cellulose, sodium carboxy methyl cellulose, methyl cellulose, polyvinyl alcohol, sodium alginate, polyethylene glycol, polyethylene oxide, chitosan, xanthan gum, tragacantha, guar gum, acacia gum, arabic gum, carrageenan, pululan, polyacrylic acid, methylmethacrylate copolymer, carboxyvinyl copolymers, and various mixtures of the above and other known water-soluble polymers, cellulose derivatives, and/or gums, among others. Other polymers that may be used include, but are not limited to, ethyl cellulose, hydroxypropyl ethyl cellulose, cellulose acetate phthalate, hydroxypropyl methyl cellulose phthalate and combinations thereof.

In some embodiments, the polymer matrix may include a surfactant to adjust the rate of dissolution and/or the surface energy of the formed construct. In other embodiments, the rate of dissolution may be adjusted by the use of a combination of high and low molecular weight polymers with or without the use of a surfactant. For example, particularly beneficial properties of film strength and disintegration profile (i.e. the rate at which the construct disintegrates upon contact with the oral cavity or other mucosa) are obtained when the water soluble components include a combination of low molecular weight polymers (e.g., those less than about 5,000 to about 60,000 daltons) and high molecular weight polymers (e.g., those of about 60,000 to about 150,000 daltons, up to about 500,000 daltons, or higher).

Various other polymers can be selected by one of ordinary skill in the art given the teachings herein and preferably includes a sufficient amount of a high molecular weight component to impart adequate strength and a sufficient amount of a low molecular weight component to facilitate the desired disintegration profile.

Additionally, one may select a single water-soluble polymer as the matrix-forming ingredient with other ingredients that assist with strength and disintegration, such as surfactants, fillers, and plasticizers. It will further be appreciated that other constituents useful in processing may be employed, including rheology modifiers. Any suitable modifiers may be used including acrylic polymer sodium salts, such as Aculyn by Dow Chemical, which is available in various grades having different molecular weights. The choice of any particular inactive formulation ingredient combination may also be dependent, in part, on its interaction with the active ingredient(s) and its influence on the properties of active ingredient(s).

According to another exemplary embodiment of the invention, films and other unit dose constructs using a water soluble low molecular weight component need not use a water soluble polymer for that component. Instead, the low molecular weight component may be other low molecular weight molecules, monomers, oligomers or a combination thereof (i.e. xylitol, glycerol, polyethylene glycol, propylene glycol, etc.). The low molecular weight component serves to promote disintegration, but is present in an amount such that strength is adequate for processing and dispensing. Various concentrations of the low molecular weight component can be utilized.

The amounts of high and low molecular weight components can be adjusted to achieve a desired disintegration profile for the film, which may range from a few seconds to several minutes or even hours. When slower disintegration is desired, the concentration of the high molecular weight component can be increased relative to the concentration of the low molecular weight component. When faster disintegration is desired, the concentration of the low molecular weight component can be increased relative to the concentration of the high molecular weight component. Additionally, the thickness and surface to volume ratio of the construct can be adjusted to achieve a desired disintegration profile. To increase the disintegration time, the thickness is increased and/or the surface to volume ratio is reduced. Adequate film strength should be maintained to allow for handling of the construct.

In addition to the active ingredient discussed immediately below, other ingredients that may be incorporated into the formulation include a plasticizer, sweetener, thickener, buffer, stabilizer, flavorings, and/or other additives and which are preferably, but not necessarily, water soluble. The types and amounts of such ingredients are familiar to those within the art for formulating dissolvable constructs in accordance with conventional methods. It will be appreciated, however, that exemplary embodiments, which employ deposition of individual, discrete unit doses, may have an overall solids or non-volatile content in the formulation that is greater than that used in conventional methods and, as a result, require less drying time. Thus, while referred to herein as a liquid formulation that is employed to form the individual unit doses, it will be appreciated that term encompasses any wet, non-solid flowable substance and in some embodiments may resemble the consistency of a paste.

Unit dose constructs in accordance with exemplary embodiments also include one or more active ingredients, typically a pharmaceutical drug. A wide range of active ingredients may be incorporated into the liquid formulation prior to formation and may be incorporated in any form, including as a solution, emulsion, suspension, or dispersion. The specific form may depend upon the particular combination of active ingredient and polymer to be employed. That is, active-containing liquid formulations that are used to create the constructs may be in the form of a solution in which all ingredients, including drug substances, are fully dissolved and soluble in the bulk liquid; as an emulsion, typically used for aqueous formulations to which an oil-soluble ingredient such as a flavoring has been added; and suspensions or dispersions in which insoluble active ingredients or other excipients may be added to the bulk-liquid formulation while still achieving uniformity of distribution in the subsequently formed construct.

Active ingredients include, by way of example and not of limitation, ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-Parkinson agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thromb otic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof. The types and amounts of active ingredients to be employed are familiar to those within the art for formulating conventional dissolvable films and tablets.

Unlike conventional methods of forming dissolvable thin films as a cast sheet that is subsequently cut into smaller unit doses, constructs in accordance with exemplary embodiments are created by direct deposition of the liquid formulation in discrete regions to form individual unit doses. Among other advantages, the use of individually formed doses limits variation of the active ingredient between dosage units that may occur across a continuous web as a result of coating thickness variations in conventional master roll film formation. This helps ensure that a relatively more precise, consistent volume of formulation and active ingredient can be deposited in directly forming smaller-scale, single unit doses.

The direct formation of unit doses may be accomplished using any suitable technique for accurately and precisely depositing a discrete amount of the liquid formulation (i.e., polymer, active ingredient, and any additives) onto a surface such that each deposition forms its own individual, unit dose construct upon drying. Exemplary techniques that may be used for the deposition include patch coating, gravure printing, screen printing, stenciling, micro-deposition, and direct dispensing, by way of example only.

Figure 1:
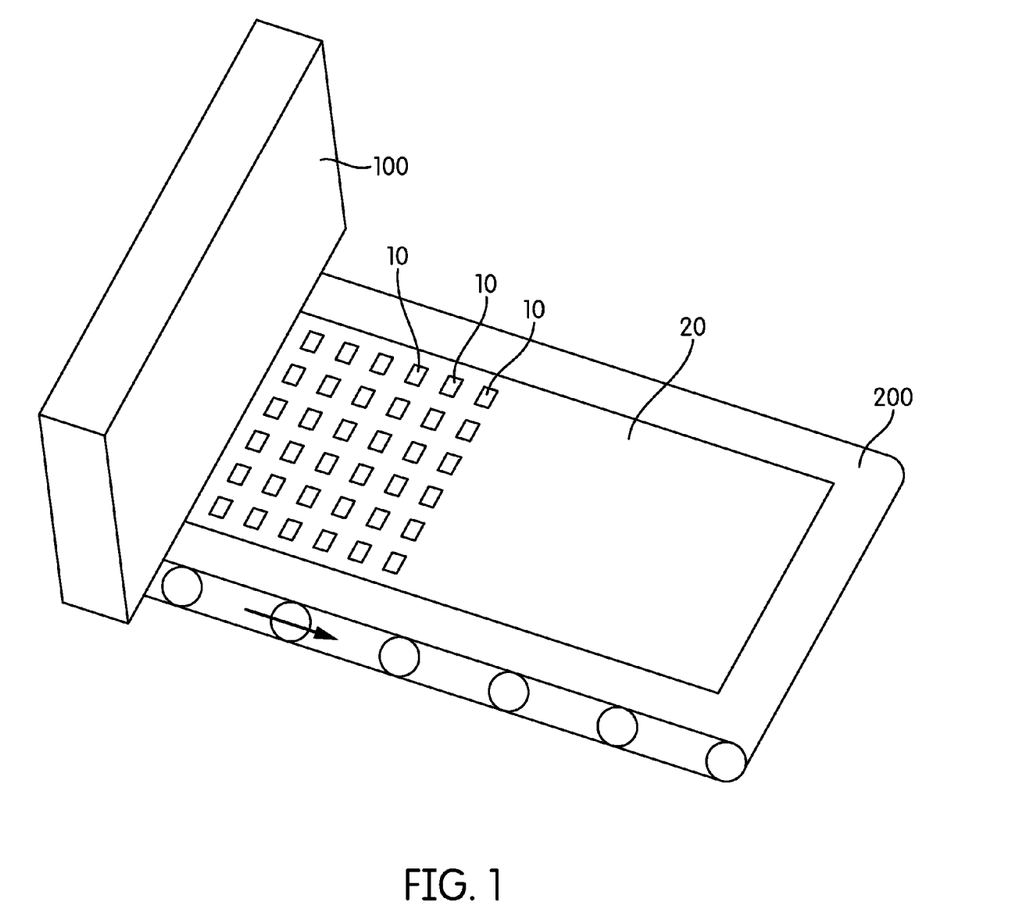
FIG. 1 illustrates an exemplary system for producing unit dose constructs in accordance with exemplary embodiments.

FIG. 1 illustrates an exemplary system for carrying out direct formation of unit dose constructs employing a depositor 100 that deposits, via a suitable unit deposition method, the muco-adhesive formulation directly onto a foil substrate 20 to form unit dose constructs 10, shown here as films.

According to certain exemplary embodiments, depositing the film in a unit dose form is accomplished by stenciling, an additive deposition process. While all forms of deposition are contemplated, stenciling has several desirable advantages over screen printing and other forms of deposition for the formation of individual discrete dosage forms. One advantage is the ability to deliver readily an appropriate deposit thickness for the construct being formed. Openings in the stencil mask define a volume of paste with which the openings in the stencil are filled. In comparison to screen printing where a mesh is used to support a mask and through which a liquid must be transferred, the stencil has no structure in the opening.

In screen printing the amount of liquid transferred to the substrate is a function of several factors including the percent open area in the mesh, the thickness of the photomask used to image the screen, the press setup (i.e. the force used to push the liquid through the screen) and the position within the screen from which the liquid breaks from the screen as it is transferred to the substrate (i.e. in most cases there is not 100% transfer of the liquid from the screen's mesh). In stenciling, the stencil mask is pressed against the substrate and the squeegee forces the liquid into the stencil opening. This fills the opening and delivers a liquid column equal to the stencil's thickness. As a result, the use of stenciling also provides a more uniform deposit of the construct formulation.

The use of stenciling in accordance with exemplary embodiments to form dissolvable thin films and other unit dose constructs is novel and introduces various challenges and concerns not faced in other, conventional, stenciling applications, but which are overcome in accordance with exemplary embodiments. Similarly, methods of directly forming individual unit doses also present challenges not present with conventional wide roll production methods of dissolvable thin films.

The equipment used for stenciling of the unit doses may be any known type used in conventional stenciling applications and generally includes a stencil frame, fill blade or squeegee, vacuum table, and a press that controls the process.

In embodiments employing stenciling, a sheet of material, typically constructed of a metal, is attached to a frame, to suspend the sheet from the frame about its perimeter. The desired image corresponding to the shape of the construct to be created is cut or etched from the sheet to form a stencil having a totally-open image. The open space is then filled with the liquid formulation (typically a paste) using a fill blade or squeegee moving across the open stencil. The thickness of the sheet of material for stenciling may be selected to correspond to the thickness of the film or other construct to be created with the stencil.

Figure 2:
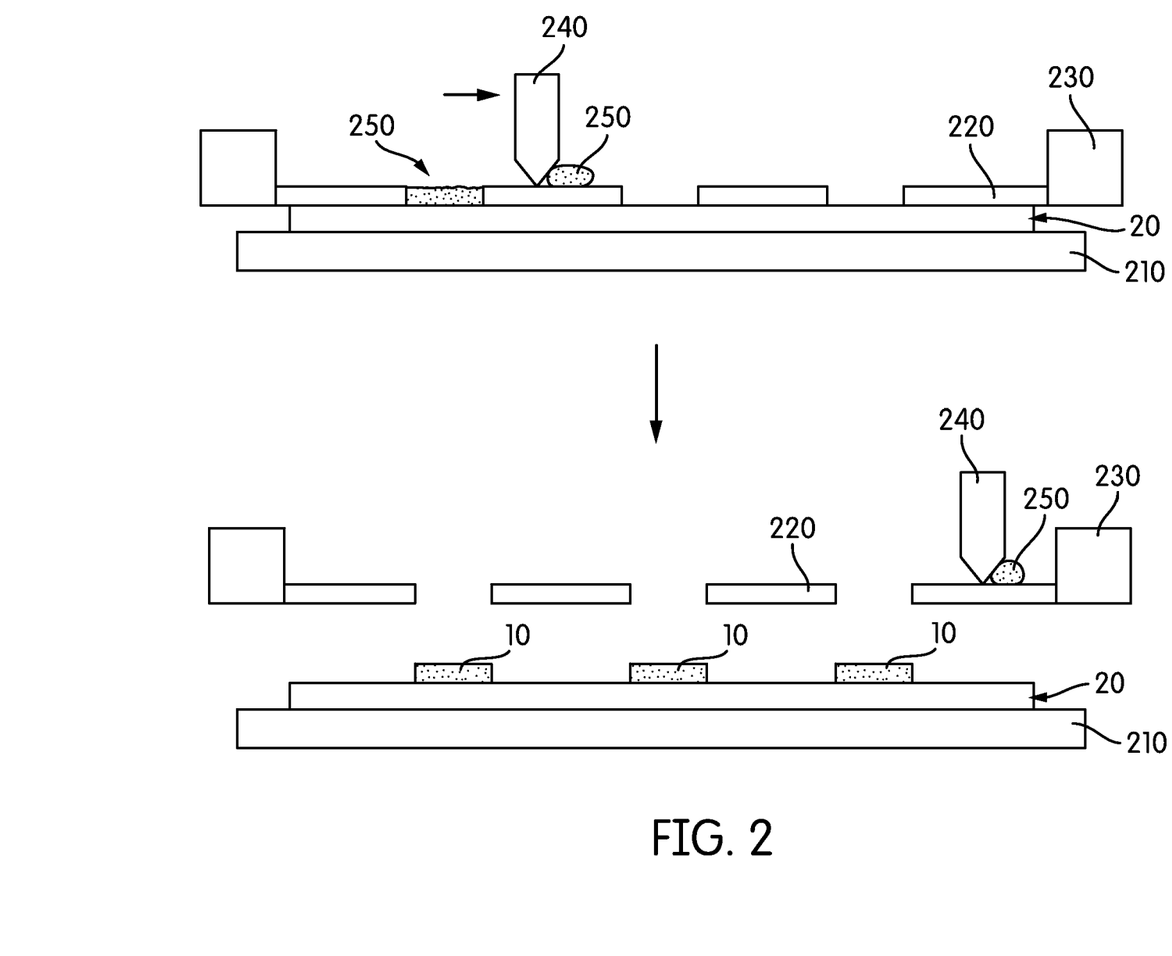
FIG. 2 illustrates an exemplary stencil set up for use in conjunction with exemplary embodiments.

FIG. 2 schematically illustrates this stenciling processing, showing a table 210 or other support, which may be disposed within the depositor 100 (FIG. 1). A stencil 220, attached to a frame 230, which is placed against a substrate (in this case the foil 20), while a squeegee 240 is used to spread a paste 250 of the muco-adhesive formulation into the openings formed in the stencil 220. Thereafter, the stencil is removed, leaving behind the paste 250 in the form of unit dose constructs 10 on the foil 20.

In the case of stenciling for the deposition of films or other constructs in individual dosage forms, the liquid muco-adhesive formulation is a composition that typically has a high solids content with a low amount of liquid carrier, with the consistency of a paste or gel. The paste is generally a thixotropic fluid with a predetermined rheology. It will be appreciated that the characteristics of a particular paste may depend upon the constituents in the formulation, as well as the shape, size and thickness of the construct to be formed. Generally, the viscosity is in the range of about 20,000 cps to about 500,000 cps, in some embodiments, in the range of about 20,000 cps to about 180,000 cps. Shear rates can vary, but are typically in the range of about 0.05 $s^{-1}$ to about 10 $s^{-1}$.

The use of a thixotropic paste is preferred as it means little or no flow occurs except when forced into the stencil by the squeegee. This enables the unit dose to better hold its shape after the stencil is removed. This helps control product uniformity in all types of constructs and is particularly advantageous when unit dose constructs are formed as thick films, wafers or tablets.

Regardless of the specific type of stenciling equipment employed, in setting up the equipment, the vacuum table should be of a uniform flatness. Preferably the flatness has a tolerance at least as fine as +/−0.0010 inches.

Care should also be taken in set-up to ensure proper positioning of the stencil relative to the substrate. As part of further set-up, the press is adjusted so both the peel and off-contact are set at or near zero for stenciling deposition of the individual unit doses. That is, any necessary adjustments should be made so that the frame of the stencil does not rise during the travel of the squeegee (i.e., "peel") and so that the stencil is in direct contact with the desired substrate (i.e., no "off-contact").

The squeegee or other blade employed in the process may be constructed of metal or any other suitable material including stainless steel or polyurethane, for example. To ensure consistent unit size (and thus consistent delivery of the active ingredient to be delivered) the blade should be straight, even and level with a uniform thickness and/or durometer hardness across its entire length. When using a polyurethane squeegee, a squeegee with a double bevel cut is preferred to yield a more uniform deposition.

It will be appreciated that the angle of the squeegee cut along the deposition angle may vary depending on the desired unit dose thickness, as well as the rheology of the paste formulation being used. It will further be appreciated that the edge definition, as well as the evenness of the paste's deposition may be dependent upon both squeegee pressure as well as the speed of travel of the squeegee across the image.

Returning to FIG. 1, which illustrates an exemplary system for carrying out the stenciling in which the stenciling (or other method of deposition) occurs within the depositor 100 that deposits the formulation directly onto a foil substrate 20 to form unit dose constructs 10, illustrated here as films as previously noted. The foil substrate 20 may advantageously be the same material that serves as primary packaging for the construct 10, which emerges from the depositor 100. The foil substrate 20 and constructs 10 may be transported along a conveyor 200. In other embodiments, the use of rolled foil may obviate the need for the conveyor by simply winding or unwinding the roll.

After the formulation has been stenciled onto the foil substrate 20, the liquid carrier in the formulation is driven off by any suitable method to yield the dissolvable construct 10. Exemplary drying methods include, but are not limited to, exposure to ambient air, infra-red (IR) heating, ultrasonic, vibration, microwave, forced air and/or hot-air systems and combinations thereof.

A benefit of depositing individual unit doses directly onto the packaging material is the ability to vacuum dry the liquid (or paste in the case of stencil deposition) formulas to form the film or other form of construct. The use of vacuum drying provides faster drying times at lower temperatures that, in-turn, affords improved productivity, lower energy consumption (less heat) and improved construct and drug stability as a result of the lower temperatures. Vacuum drying also yields a better content uniformity and patient dosing by reduced potential for entrapped air or bubble defects. Improved productivity can be achieved by drying more quickly at lower pressures as well as affording integration of other product conversion steps as part of an overall, in-line process sequence. As with other drying methods, vacuum drying may be carried out contemporaneously with one or more of the other drying methods previously discussed. Additionally, in some embodiments, vacuum drying is carried out in combination with cooling, to achieve a lyophilization effect on thicker constructs, such as tablets. As referred to herein, vacuum drying means any pressure less than ambient atmospheric, including zero torr. That is, vacuum drying encompasses both partial and full vacuum.

Vacuum drying is not used with drying conventional thin film manufacture for a variety of reasons. Conventional techniques employ relatively wide, long, continuous rolls of paper or polymeric film (e.g. polyester) release liners and the process is a continuous, constantly moving web. Accordingly, for a vacuum to be achieved the film must be encapsulated and sealed from the surrounding environment for air to be effectively evacuated. Because the coated web is continuously in motion during the formulation coating and subsequent drying process, encapsulation and air removal are not feasible in conventional thin film coating processes. Furthermore, the backing substrates or release liners typically employed may not serve as an effective air barrier thereby compromising the encapsulation effectiveness, particularly for paper release liners. The inherent flexibility of conventional release liner coating substrates adversely affect the quality of the thin film coatings during air evacuation for lack of enough mechanical integrity or stiffness to prevent distortion as air is removed by the vacuum pump.

Exemplary embodiments are not so limited and vacuum drying techniques are readily employed. In one embodiment, individual thin film unit dose constructs are stenciled in an array on a stationary but continuous web of packaging foil as described with respect to FIG. 1. Following deposition of that array by stenciling, the web is advanced a pre-determined distance upon which another array is then formed by stenciling on the web at a different location. While the second array is being deposited, a vacuum encapsulation fixture is lowered over the first array using the packaging foil as the base of the enclosure within which vacuum is applied. Some heat may also be applied if needed or desired. After deposition of the second array and drying of the first, the vacuum is relieved and the encapsulation fixture is raised or removed. The web is advanced and the process proceeds in a step-and-repeat manner, with the second array subjected to vacuum drying with the encapsulation fixture while a third layer is stenciled.

It will be appreciated that the packaging foil may be held in place during the encapsulation process to reinforce it against collapse when the vacuum is applied. For example, application of a vacuum may be applied to the opposite, underlying side of the foil (i.e., opposite from that on which the formulation was deposited). The resulting applied suction may be accomplished, for example, using an array of holes in a flat metal plate that firmly holds the foil in place prior to positioning of the vacuum fixture and vacuum application.

After the films or other form of unit dose constructs 10 are dried, a top layer of foil (not shown) or other packaging material is applied to protect them prior to use. Although the constructs are individually formed, the foil substrate and the top layer of foil are typically continuous webs that can thereafter be sealed and cut into individual packages, each containing a single construct.

Regardless of the specific drying method used, it is advantageous to carry out the drying step in a controlled atmosphere. In certain embodiments, the drying is conducted in a nitrogen or other reduced oxygen or oxygen free environment. Reducing exposure to oxygen provides the benefit of limiting oxidative degradation to which many active pharmaceutical ingredients are susceptible, resulting in greater stability of the formed construct. Such an environment may be achieved, for example, by processing in a nitrogen filled production setting (e.g. while drying) or by directing a flow of nitrogen gas over the constructs 10.

In other embodiments, in combination with or separate from the use of a nitrogen environment, the controlled atmosphere includes maintaining a low humidity throughout film processing. A relative humidity of below 45%, typically 40% and more preferably below 35%, results in the constructs having less tack, aiding in the ability to be more easily removable from their package.

Yet another advantage of stenciling is that the rheology does not have to be tuned to produce a level deposit. In screen printing, the liquid film formulation must move through the mesh openings, then flow out after the screen moves away to produce a smooth deposit across the image. Failure to flow would result in screen mesh marks appearing in the deposit. In stenciling, the squeegee itself acts to level the deposit of the formulation as it moves across the opening.

Furthermore, the generation of an aesthetically acceptable deposit in terms of its appearance is readily accomplished with stenciling. Moving liquid film formulations across a mesh screen results in a significant amount of air being entrained in the fluid that remains when the deposited film formulation is cured. With stenciling, this issue is minimized because the liquid, or paste, is pushed across a smooth stencil plate. Additionally, screen printing is usually done by pushing the liquid across the screen twice to deliver a screen printed image (flood/print), while the liquid is pushed across the stencil only once for stenciling (print/print).

The deposition of individual, discrete unit doses by stenciling or otherwise also affords the possibility of an infinite number of design shapes. In particular, design shapes that enhance disintegration times but without yield loss or additional cost associated with die cutting into those shapes can be achieved, as well as the ability to form complex shapes that would be impractical or impossible to form by die-cutting. For example, a film or other type of unit dose construct may be directly formed as a donut or oval with a hole in the center that increases the surface area of the film available for dissolution by saliva. In other embodiments, simply providing more traditional shaped rectangular constructs, but with rounded edges aids in removability from the package.

Figure 1A:
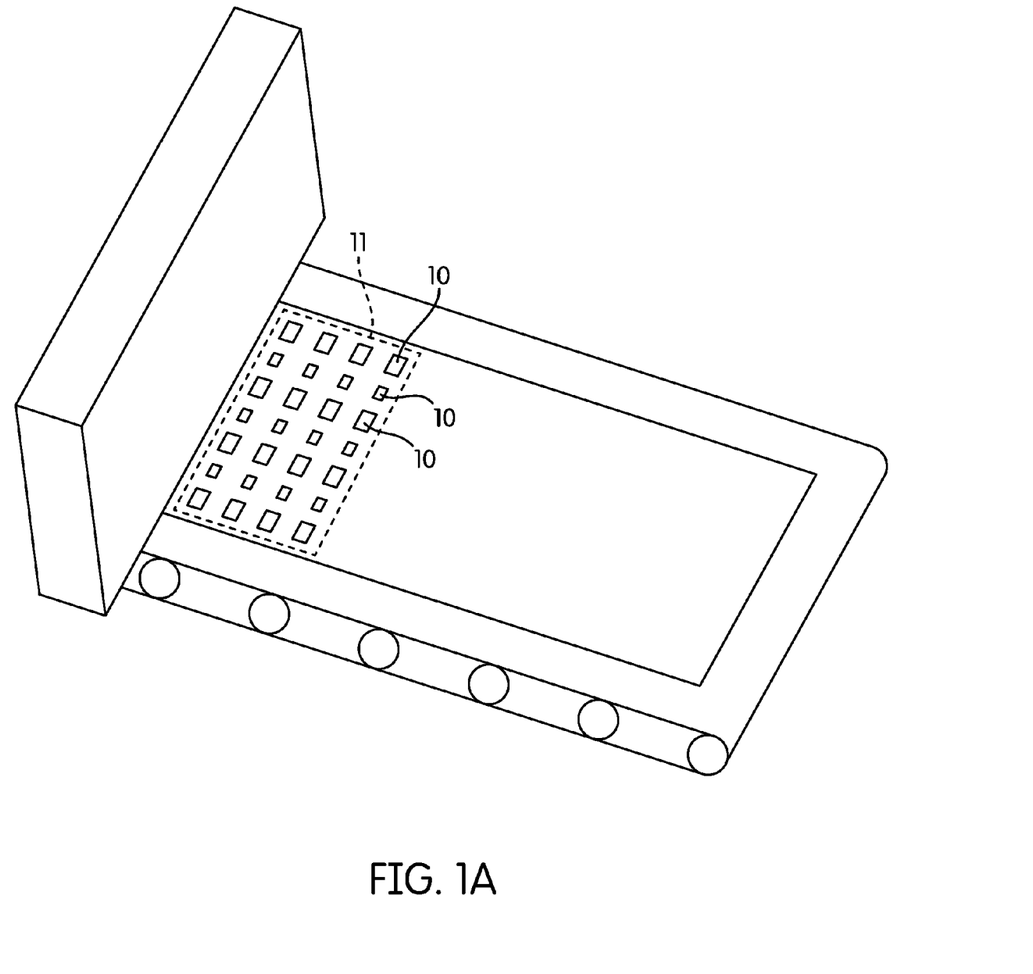
FIG. 1A illustrates an exemplary system for producing unit dose constructs in accordance with an exemplary embodiment showing deposition in regimen format.

Another advantage that can be achieved with exemplary embodiments is the ability to create a product that corresponds to a particular regimen in which, for example, a multi-week supply of a particular product is prepared at once. For example, if the regimen calls for variations in strength depending upon the day, a row of seven can be deposited with the size of each film or other construct 10 within that row varied based on the called upon regimen as illustrated in FIG. 1A, which shows four rows of seven films (i.e. four weeks), with a variation in size in the row corresponding to the amount required on a particular day. Each regimen may then be sealed, segregated and marked; the regimen may be formed as a single packet 11 with individual packages separately sealing the films of the regimen, the packages being separable from one another, such as by perforation, for later separation and opening by the user.

Yet another advantage associated with exemplary embodiments is the avoidance of yield losses associated with conventional dissolvable film production processes. Current continuous master roll production used in conventional processes includes start-up and end-of-roll losses that, on a percentage basis, increase as the coating length is reduced. Furthermore, the master roll typically has an edge that has to be trimmed and removed in a post-coating, roll-slitting process. Additional yield losses occur when the slit rolls are subjected to a die-cutting process to produce the individual finished unit doses. There are start-up losses during the die-cutting and packaging process as the manufacturer sets up the machine to coincide with unit placement and heat-sealing of the individual primary package. Because the formulations used to create the film generally contain relatively expensive pharmaceuticals, these yield losses represent a significant cost.

Accordingly, by forming individual unit doses in accordance with exemplary embodiments, these types of yield losses are avoided. Furthermore, reconciliation for controlled substances is easier; diversion of controlled substances becomes more obvious and recognizable in the manufacturing supply chain because less of the controlled substance is lost as waste in the trimming process that can introduce difficulty in accounting for other sources of drug loss.

As briefly noted earlier, conventional methods of dissolvable thin film production use a master roll cast onto a paper or polyester substrate (with or without a release layer) that serves purely as an in-process and handling aid that adds no direct product value. Instead, it represents an additional cost as the liner is removed and discarded during downstream die-cutting of the individual dosage units from the master roll. Exemplary embodiments eliminate the need for the liner processing aid, as well as the slitting and individual dosage unit die cutting steps. Instead, individual unit doses of the liquid formulation containing the active ingredient are deposited directly onto the foil substrate 20 that is the ultimate packaging material. Unit dose packaging may be accomplished directly after unit dose deposition and drying as an extension of the unit dose deposition process.

In some exemplary embodiments, the releasability of the unit dose construct 10 from the packaging foil (i.e. the foil substrate 20) is enhanced. One manner in which this is achieved is by providing a surface treatment and/or release coating on the surface of the foil substrate 20 to which the constructs 10 are deposited. Exemplary surface treatments include a laminate foil having a layer applied to its surface composed of a material that is tailorable to exhibit different levels of surface energy via, for example, chemical composition or treatment. An examples of such materials includes polyethylene homopolymer and ethylene vinyl acetate (EVA) copolymers ranging from 100% polyethylene to 60% polyethylene/40% vinyl acetate (by weight), in which the surface energy is modified by adjusting the amount of vinyl acetate present in the composition. Surface energy may also be tailored by subjecting the foil (or foil laminate) to radiation, corona discharge, plasma, or other known techniques for modifying surface energy. The surface energy modification can be over the entire substrate surface or over one or more distinct regions may be applied in a repeating pattern or at specific, discrete locations.

Figure 3:
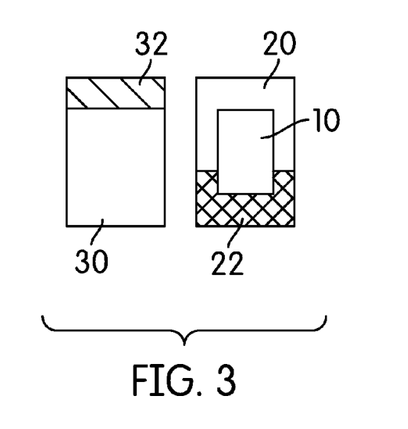
FIG. 3 illustrates a package for a unit dose construct in accordance with an exemplary embodiment.

Turning to FIG. 3, in one embodiment a unit dose construct 10 is formed on the foil substrate 20 that forms the bottom of the package as described above with respect to FIG. 1. While the entire foil substrate 20 may include a release coating or other surface treatment, in this embodiment a smaller region 22 (shown in cross-hatch for purposes of illustration) of the foil substrate 20 has a release coating or surface treatment that results in construct adhesion in that region 22 that is lower than the rest of the substrate 20.

The package is sealed by a top foil layer 30 applied over the construct 10 to form the package and seal it from the surrounding environment. The top foil layer 30 may also be surface treated or have a release coating over its entirety or in one or more identified regions. Like the foil substrate 20, the top foil layer 30 is also illustrated with a region 32 (shown in cross-hatch for purpose of illustration) with a surface tension that differs from the rest of the top foil layer 30 by employing, for example, a different release coating or a different type or amount of surface treatment. In this embodiment, that region 32 is the only portion which has any adhesion to the construct 10 and that adhesion is greater than that of the construct to the foil substrate 20.

As a result, when the top layer 30 and the foil substrate 20 (which would be overlying one another to form the package, but are shown side-by-side for purposes of illustration and discussion) are separated from one another by an end user, removing the top layer 30 from the foil substrate 20 lifts the construct 10 from the foil substrate 20. This helps the user easily grasp and remove it from the package.

It will be appreciated that FIG. 3 shows a separated single unit dose package for purposes of illustration. In the context of the continuous process illustrated in FIG. 1, the roll of foil used for the foil substrate 20 is provided with regions of differing surface tension established in advance according to a particular pattern that achieves the desired result, which may be specific to the size and other parameters of the construct 10 being manufactured, and thus where it is deposited on the substrate 20 with respect to those regions. Alternatively, the surface energy modifications, tailoring or patterning can be accomplished as an integral part of the deposition process, i.e., as part of an inline treatment process of the foil during construct production.

Alternatively, or in combination, the surface energy of the formulation being deposited can also be modified or tailored to achieve a desired release characteristic after deposition.

The modification of surface energies of the substrate and/or the formulation is primarily with respect to release characteristics, as the use of a thixotropic paste in forming the unit doses results in low flow in the absence of a shear force. Nevertheless, in some embodiments, surface energy modification may also be employed to result in better wetting by the unit dose formulation. In one embodiment, a corona- or plasma-treatment using the stencil prior to formulation provides a region on the substrate surface of increased surface energy that promotes fluid migration. In another embodiment, the surface energy of the formulation being stenciled can be modified or tailored to achieve a desired flow characteristic during and after stenciling.

In addition to improvements in the manufacturing of thin films and other unit dose constructs, the use of stenciling or other unit deposition methods to deposit discrete amounts of the formulation also provides an ability to achieve improvements in the unit dose constructs themselves.

Some drug delivery films employ a two layer film in which a first layer contains a formulation containing the active ingredient and a second layer serves as an inactive backing layer or a layer containing a different active ingredient or the same active ingredient at a different concentration. The second or backing layer may be the same or a different formulation as the first layer, except that it does not otherwise contain the same active ingredient or same level of active ingredient found in the first layer. The backing layer may serve as a barrier against flow of the active ingredient into the oral cavity and the gastro-intestinal tract. A significant drawback to making such films in the conventional manner is that their wide web production process requires the first and second layers to be of the same area, formed as overlying webs in which one of the layers is coated via a second, separate casting or laminating step on top of the other layer.

In addition to requiring first and second layers of the same area, this process also still results in a master roll that requires slitting into narrower width roles coupled with removal of the beginning and end of the rolls to achieve defect-free slit rolls of uniform coated layer thickness. These same considerations apply to situations calling for more than two layers.

Figure 4:
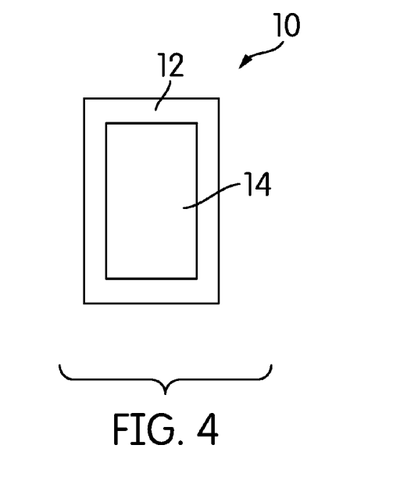
FIG. 4 illustrates a unit dose construct in accordance with an exemplary embodiment.

Exemplary embodiments employing unit dose deposition overcome these drawbacks by providing a multi-layer film or other unit dose construct that includes stenciling a smaller area of the active layer within a larger area defined by the backing layer (ordinarily following an intermediate drying step). This can be used to create a window or picture frame effect as shown in FIG. 4, in which the illustrated film 10 is multiple layers, containing an underlying backing layer 12 and a smaller, overlying active layer 14. The backing layer 12 thus provides a peripheral seal around the active layer 14 when the film 10 is applied to mucosa. This can prevent leakage of the active ingredient from the periphery of the active layer 14 into the oral cavity and further helps to ensure that all of the drug or other active ingredient is delivered via the desired mucosal pathway.

In addition, the use of the window frame can be used to effectively seal the active layer 14 and thereby mask an offensive taste due to the active ingredient. The backing layer 12 prevents leakage of the drug from the active layer 14 into the oral cavity where perceptible taste would occur.

A further advantage over conventional two layer films is that by depositing the active layer 14 in discrete unit doses onto the backing layer 12, enhanced dose accuracy and uniformity between films or other constructs 10 is achieved because a consistent, precise volume of the active liquid construct formulation is applied independent of area or thickness of the backing layer.

Conversely, in conventional wide web film manufacture, deposition thickness characterization is typically accomplished by characterizing the weight deposited per unit area (i.e. "coating weight" sampling); while process parameters are typically adjusted at the front end of a coating campaign and then maintained after the desired target is achieved, the precision of the coating weight of the active layer is affected by variability in the thickness of the underlying backing layer. For example, a depression in, or thinning of, the backing layer would result in a localized area of greater thickness of the active layer. This concern can be overcome in certain exemplary embodiments because each active layer 14 may be individually measured and stenciled as a consistent volume regardless of any variation in the backing layer 12 to which it is applied. It will further be appreciated that exemplary embodiments may also be used to deposit discrete active layers onto a backing layer that is a continuous web, although that would have the effect of re-introducing certain trimming and other conversion steps in manufacturing.

Figure 5A:
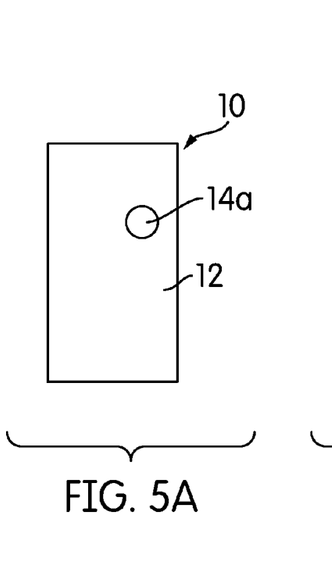
FIGS. 5A and 5B illustrate a unit dose construct in accordance with another exemplary embodiment.
Figures 5B, 6:
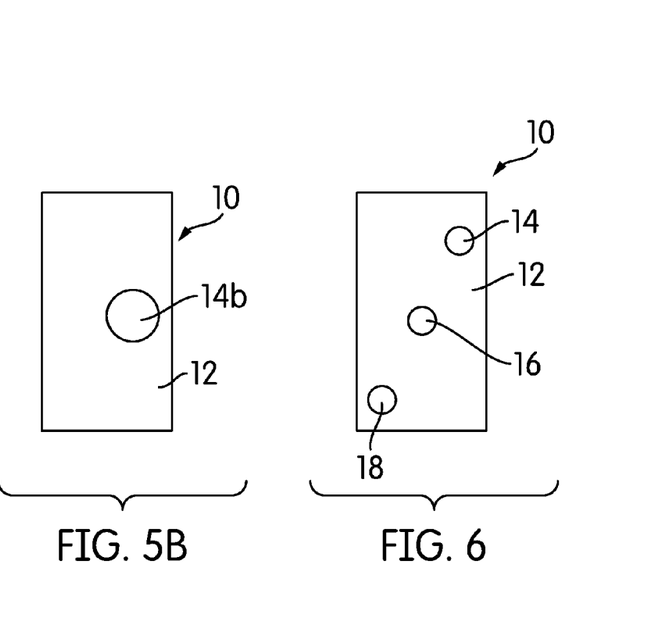
FIG. 6 illustrates a unit dose construct in accordance with an exemplary embodiment.

Stenciling the active layer 14 as an individual unit dose to individually formed backing layers 12 also affords flexibility that permits variation in the size of the active layer 14 within the area defined by the backing layer 12. Turning to FIGS. 5A and 5B, in certain embodiments different dosage strengths can be achieved by depositing smaller or larger active layers 14a,b on the backing layer 12. Thus, the same size backing layer 12 can be used to deliver the same size construct 10 across multiple dosage strengths. Conversely, the same size active layer 14 can be used with different sized backing layers 12 that can be modified to meet a particular class of users' ability to handle the unit dose construct, particularly in the context of films, which may be independent of the amount of active ingredient to be employed (i.e., larger films may be desired for pediatric or geriatric patients). This may also be of particular benefit for low dosage and/or particularly potent drugs which, if used alone without a backing layer, would require a unit dose area so small that the resulting unit dose construct would otherwise be too difficult to handle.

As shown in FIGS. 5A and 5B, two constructs 10 are formed with a uniformly sized backing layer 12. In the first construct 10, a small active layer 14a is applied to the backing layer 12, for example, for use in a pediatric size dose of the active ingredient that in the context of this example, still provides a film that, by virtue of the size of the backing layer 12, is large enough to be easily handled. For an adult size dose, that same backing layer 12 is used with a larger active layer 14b deposited thereon to deliver a larger amount of the active ingredient, with the same size film. Because the area of the active layer can be adjusted, the same formulation can be used for both the pediatric and the adult dose.

An additional benefit achieved by exemplary embodiments that use the same size backing layer 12 for active layers 14a, 14b of different size is standardization of the overall construct size across multiple dosage strengths. As a result, tooling and packaging can also be standardized with respect to the same overall size defined by the area of the backing layer 12.

It will be appreciated that in some embodiments, it may be desirable to incorporate additional ingredients into the active layer formulations used to produce active layers 14*a*, 14*b* of different dosage strengths to more easily differentiate between them. For example, while the overall size of the doses containing the active layers 14*a*, 14*b* may be different, they might still be visually similar. Differentiation may be achieved, for example, by the use of different colors for active layers of different strengths. Colorants may also be used to distinguish films 10 or other unit dose constructs having different active ingredients, even if the size or strength of the dosage is the same.

FIG. 6 illustrates yet another exemplary embodiment. In some cases, two active-drugs must be conveyed to a recipient at the same time. This may be achieved by combining two different active ingredients in the active-layer formulation. However, that combination may not be possible in many circumstances such as, for example, where the active ingredients are incompatible (e.g., they react or degrade when in contact with one another).

Exemplary embodiments of the invention overcome this problem by providing a construct 10 that employs a single backing layer 12 on which multiple different active layers 14, 16, 18 containing different active ingredients can be separately and individually stenciled in discrete regions of the backing layer 12. This maintains separation between incompatible active ingredients, which can thus be isolated from one another up to the point of administration (i.e., ingestion, etc.).

Another advantage of exemplary embodiments, which provide for the production of unit dose constructs containing two or more layers and including different APIs positioned adjacent one another in the same construct is that such an approach is not possible in conventional means of forming orally disintegrating tablets (ODTs) such as tablet pressing and/or lyophilization. If a tablet coating is applied, it will surround the tablet core by traditional manufacturing methods. This does not allow for maintaining two separate layers that provide unidirectional drug release.

EXAMPLES

The invention is further described by way of the following examples, which are presented by way of illustration, not of limitation.

Example 1

An aqueous placebo formulation was formed with 19.4% solids including the following ingredients: hydroxypropyl methylcellulose, polyethylene oxide, disintegrant, buffering agents, sweetener, flavor and a colorant. The viscosity when it was measured using a small-sample Brookfield spindle was found to be approximately 57,600 cps at 4 $s^{-1}$.

Example 2

The formulation in Example 1 was dispensed directly onto a foil substrate (Alcan DM8964 peelable foil) using a stencil and a stencil press. The stencil thickness was 0.035". Stencil openings were 1"×2" in an 18-up format. Once the formulation was deposited onto the foil, it was dried using a gas forced-air oven at 70° C. for 8 minutes.

Example 3

An aqueous formulation was formed with 22% solids including the following ingredients: hydroxyethyl cellulose, hydroxypropyl cellulose, buffering agents, sweetener, flavor, preservatives and colorant. The viscosity when it was measured using a small-sample Brookfield spindle was found to be approximately 25,000 cps at 0.05 $s^{-1}$.

Example 4

An aqueous formulation was formed with 11% solids including the following ingredients: sodium carboxymethyl cellulose, hydroxyethyl cellulose, hydroxypropyl cellulose, polyacrylic acid, buffering agents, sweetener, flavor, preservatives and an active ingredient. The viscosity when it was measured using a small-sample Brookfield spindle was found to be approximately 12,000 cps at 0.05 $s^{-1}$.

Each of Examples 3 and 4 were also formed into unit dose constructs as described in Example 2.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims and all other patentable subject matter contained herein.

The invention claimed is:

1. A method of forming a dissolvable unit dose construct comprising:
    providing a muco-adhesive composition comprising a polymer matrix, the polymer matrix comprising a water soluble polymer, the composition further comprising an active ingredient and a liquid carrier; and
    depositing the composition onto a foil substrate as a plurality of individual dosage units; and
    removing at least a portion of the liquid carrier from the individual dosage units, wherein the foil substrate is a treated foil substrate having a modified surface energy on the side on which the composition is deposited.

2. The method of claim 1, wherein a first area of the treated foil substrate has a modified surface energy on the side on which the composition is deposited that is lower than a surface energy of a second area on the side of the treated foil substrate on which the composition is deposited.

3. The method of claim 1, wherein the step of removing liquid carrier includes drying the composition by the application of heat, vibration, ultrasound, or a combination thereof.

4. The method of claim 1, wherein the composition is provided as a thixotropic paste having a viscosity in the range of 20,000 cps to 500,000 cps at a shear rate in the range of 0.05 $s^{-1}$ to 10 $s^{-1}$.

5. The method of claim 1, further comprising, after the step of depositing, depositing a second composition to form multi-layered individual dosage units.

6. The method of claim 1, wherein the step of depositing includes depositing the paste onto the foil substrate in a predetermined geometric shape having at least three sides.

7. The method of claim 6, wherein the predetermined geometric shape includes a rounded corner.

8. The method of claim 1, wherein the water soluble polymer comprises cellulose or a derivative thereof.

9. The method of claim 1, wherein the active ingredient comprises a pharmaceutical drug.

10. The method of claim 1, comprising depositing adjacent individual unit doses having different areas.

11. The method of claim 1, wherein the individual dosage units are dissolvable films.

12. The method of claim 1, wherein the individual dosage units are tablets or wafers.

13. The method of claim 1, wherein the step of removing is carried out in an atmosphere having a lower oxygen content than air.

14. The method of claim 1, wherein the step of removing is carried out in an atmosphere having less than 45% relative humidity.

* * * * *